United States Patent [19]

Habekost

[11] Patent Number: 4,960,132

[45] Date of Patent: Oct. 2, 1990

[54] SELF-CONTAINED PERIODONTAL PROBE FOR REMOTE RECORDATIONS

[76] Inventor: Charles F. Habekost, 463 Curie Dr., San Jose, Calif. 95123

[21] Appl. No.: 403,108

[22] Filed: Sep. 5, 1989

[51] Int. Cl.⁵ .................................................. A61B 5/10
[52] U.S. Cl. ...................................... 128/776; 433/72; 33/514
[58] Field of Search ................... 128/776, 642; 606/39; 33/514; 433/32, 72, 215, 31

[56] References Cited

U.S. PATENT DOCUMENTS

| | | | |
|---|---|---|---|
| 3,058,225 | 10/1962 | Ward | 33/172 |
| 3,297,021 | 1/1967 | Davis et al. | 128/2 |
| 3,543,405 | 12/1970 | Banhart | 32/26 |
| 3,559,292 | 2/1971 | Weissman | 33/169 |
| 3,943,914 | 3/1976 | Grenfell et al. | 128/2 |
| 4,340,069 | 7/1982 | Yeaple | 128/776 |
| 4,463,759 | 8/1984 | Garito et al. | 128/303.14 |
| 4,677,756 | 7/1987 | Simon et al. | 33/514 |
| 4,791,940 | 12/1988 | Hirschfeld et al. | 128/776 |

FOREIGN PATENT DOCUMENTS 8905117 6/1989 PCT Int'l Appl. ................. 128/776

Primary Examiner—Max Hindenburg
Assistant Examiner—Robin R. Longs
Attorney, Agent, or Firm—Thomas Schneck

[57] ABSTRACT

A periodontal probe which is structurally isolated from a recording device and which is touch-activated. The probe includes a tubular probe body and a semi-rigid fiber extending from a forward segment of the probe body for insertion into an anatomical pocket of a patient. A slider member within the probe body is connected to the fiber at one end and to an iron-nickel core at the opposite end. The fiber is inserted into an anatomical pocket in a fully extended position. After contact with the base of the pocket, the fiber begins to retract into the probe body. Thus, the fiber and the core move relative to the probe body. The probe body is brought into contact with the upper extent of the anatomical pocket, so that the portion of the fiber extending from the probe has a length equal to the depth of the pocket. The core is received within a coil winding, and the relative position of the core within the coil winding determines the inductance of a LC oscillator. Consequently, the frequency of the oscillator varies with the extension of the fiber from the probe body. The oscillator is connected to a timer which controls current through an infrared LED. Output from a timer is triggered by the operator of the periodontal probe merely by making contact with an electrically isolated region on the probe body. Finger contact causes a change in capacitance at the isolated region to activate the transmission of data.

17 Claims, 3 Drawing Sheets

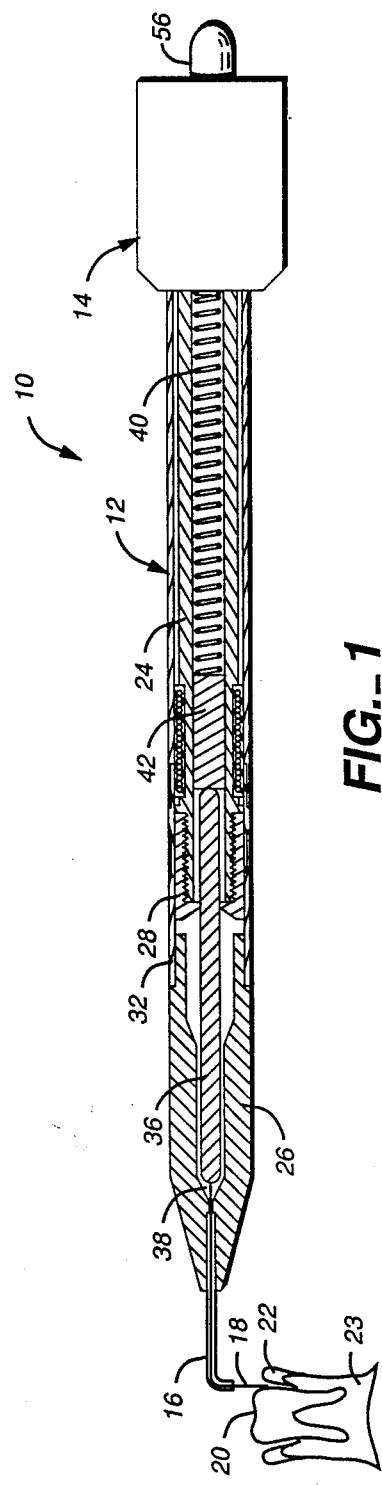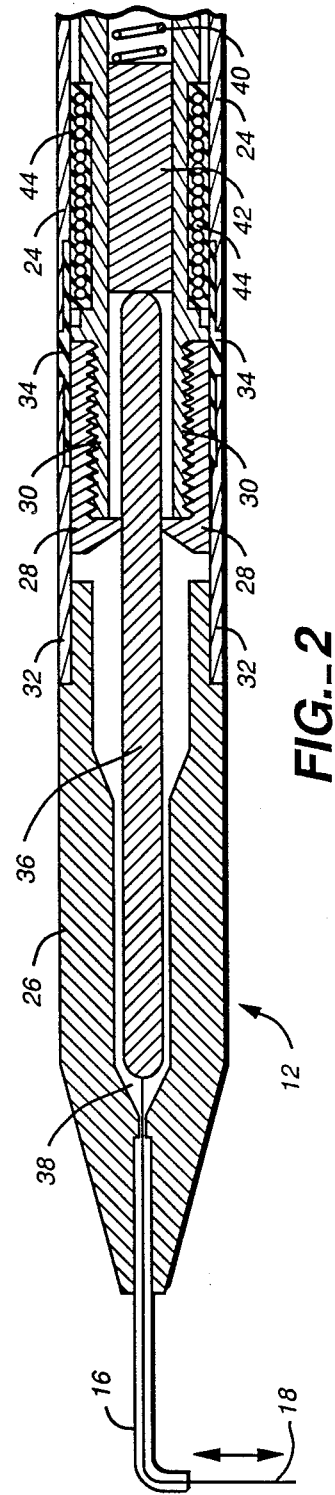

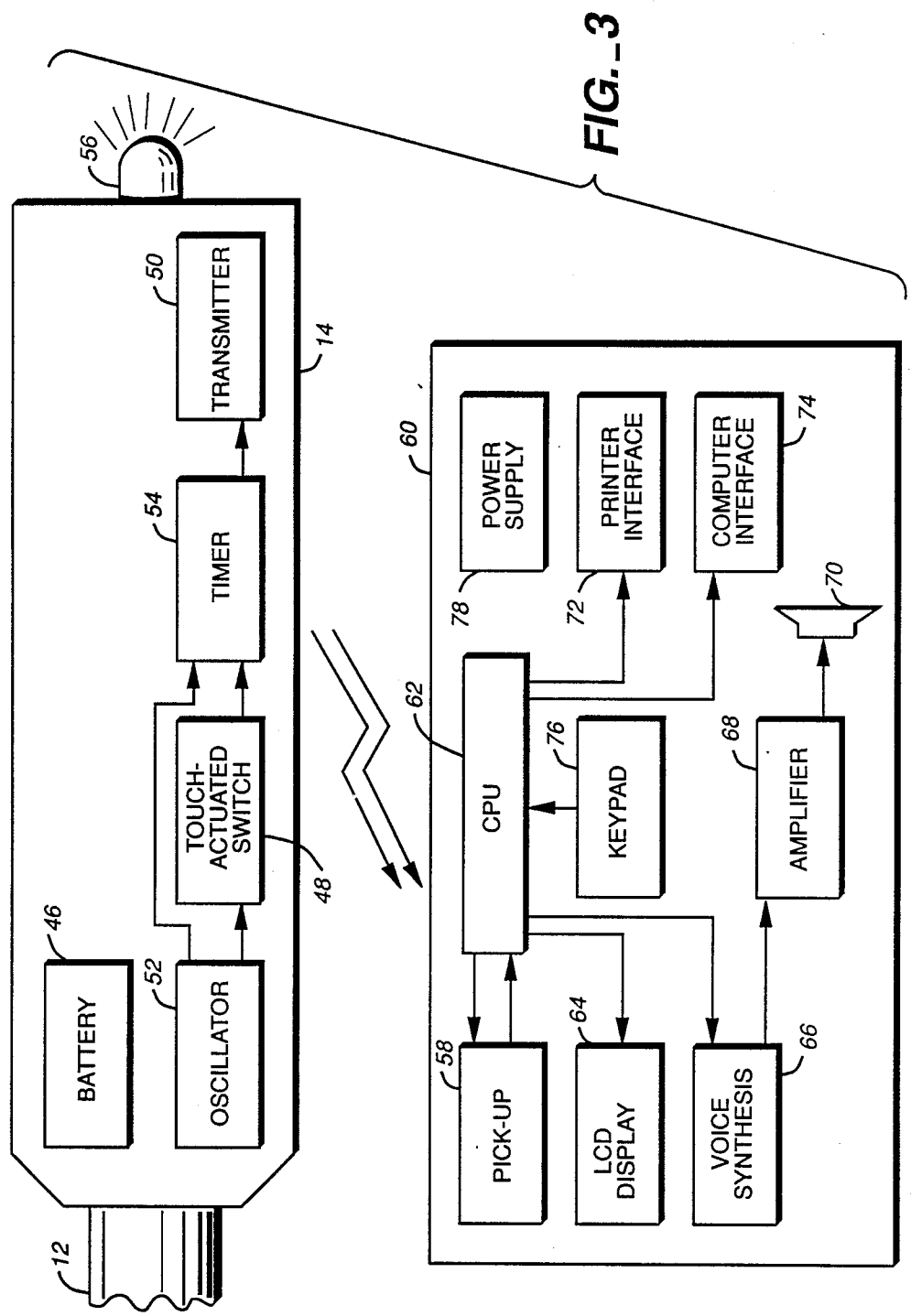
FIG._3

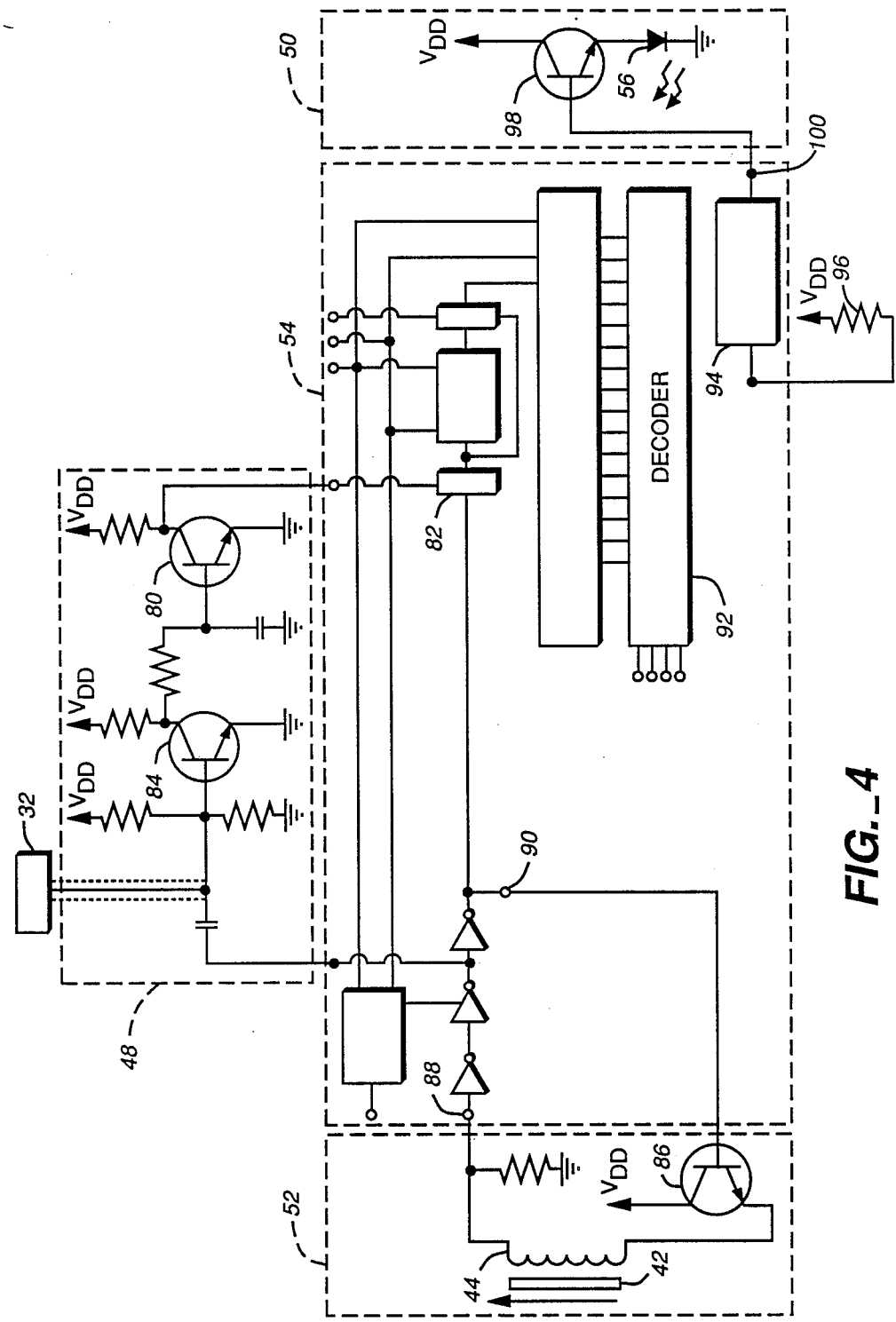
FIG._4

SELF-CONTAINED PERIODONTAL PROBE FOR REMOTE RECORDATIONS

TECHNICAL FIELD

The present invention relates to medical and dental apparatus and particularly to apparatus for determining the depth of an anatomical pocket.

BACKGROUND ART

Periodontal probing is the clinical measurement of the depth of the gingival sulci of a dental patient. The gingival sulci are the spacings between the patient's teeth and gums. Periodontal probing is an established criteria for the diagnosis and treatment of diseases such as gingivitis and pyorrhea.

Originally, periodontal probing devices comprised a handle having a probe tip attached either directly to a mechanical indicator or indirectly, via electrical circuitry, to an electrical meter or the like located on the probe handle. Such a device is described in U.S. Pat. No. 3,058,225 to Ward. A different approach is described in U.S. Pat. No. 3,943,914 to Grenfell et al. The Grenfell et al. patent teaches that because the depth measurement is indicated on the probe handle itself, a dentist must either measure and then record individual measurements by hand or employ an assistant to do the recording. Because typically six measurements are taken for each tooth, a complete examination of a person having all thirty-two teeth would be extremely time consuming. Thus, Grenfell et al. teaches use of a foot pedal to activate a recorder console attached to the periodontal probe by a cable.

The combination of a periodontal probe, a foot pedal switch and a recording device, all linked together by cables, overcomes some of the problems associated with prior approaches of periodontal probing. However, such an arrangement limits the maneuverability of the depthmeasuring apparatus. The lack of maneuverability is often merely an inconvenience, but may be objectionable where dentists would find it otherwise advantageous to share the apparatus. Moreover, the requirement of remaining in contact with a foot switch, and the resulting requirement that there be an operator weight shift to activate the foot switch, may jeopardize the accuracy of periodontal measurements which typically are only in the range of 1–3 mm.

An object of the present invention is to provide a probe for the measurement of the depth of an anatomical pocket, wherein manipulation and portability of the probe are facilitated.

DISCLOSURE OF THE INVENTION

The above object has been met by a probe which is structurally isolated from a recording device and which is touch-actuated to aid in protecting against measurement inaccuracies which can occur where the actuation procedure is more rigorous. The probe includes a tubular probe body having an arcuate sleeve at a forward end. A semi-rigid fiber is slidably received by the sleeve and has a lead portion which extends from the sleeve for insertion into an anatomical pocket of a patient.

A transducer is operatively coupled to the fiber for generation of a signal having a frequency precisely related to the depth of the anatomical pocket. The transducer includes a coil winding fixed within the probe body and includes a core attached to the fiber by a slider member. Motion of the fiber is thereby translated to the core. The position of the core relative to the coil winding determines the inductance of an inductor which is an element of an LC oscillator, and consequently determines the frequency of the oscillator as the core position varies with the extension of the fiber from the sleeve.

The oscillator is connected to a pulse generating timer which controls current through an infrared light-emitting diode (LED). The timer generates pulses at a time interval determined by the frequency of the oscillator. The infrared LED functions as a transmitter to radiate data to a remote receiver. That is, the probe is structurally isolated from the receiver Preferably, the remote receiver includes a voice synthesizer to audibilize the reading of pocket depth while simultaneously making a written recordation.

Output from the timer is triggered by the user merely making contact with an electrically isolated region on the probe body. Finger contact causes a change in capacitance at the isolated region to activate the transmission of data.

An advantage of the present invention is that the probe body is a self-contained unit so that the probe may be easily transported. It is possible to equip each area in which the probe may be used both with a pickup element, such as a photodetector, to receive the pulses of the transmitter and with a speaker to audibilize the depth measurements. Another advantage is that the probe is not restricted by connection to a cable, thereby facilitating repositioning of the probe to measure pockets associated with less accessible teeth.

A third advantage is that the measurements are touch-actuated. The capacitance-change switch requires a mere contact of an operator's finger with the isolated region of the probe body. Typically, a periodontal pocket has a depth of less than 5 mm, and a sudden weight shift or body movement to actuate a depth measurement would have the tendency to jeopardize the accuracy of such a measurement. The touch-actuated switch greatly reduces the risk of measurement inaccuracies resulting from operator movement at the critical moment of measurement.

BRIEF DESCRIPTION OF THE DRAWINGS

FIG. 1 is a side, cutaway view of a periodontal probe in accord with the present invention.

FIG. 2 is a side sectional view of the front portion of the probe of FIG. 1.

FIG. 3 is a block diagram of a depth measurement system using the periodontal probe of FIG. 1.

FIG. 4 is a schematic diagram of the periodontal probe of FIG. 3.

BEST MODE FOR CARRYING OUT THE INVENTION

With reference to FIGS. 1 and 2, the periodontal probe 10 is shown as having a tubular probe body 12 and a logic housing 14. Press fit into the forward end of the probe 10 is a sleeve 16 having an arcuate tip to facilitate an insertion of a fiber 18 into a periodontal pocket between a tooth 20 and a gum 22 of a patient. The fiber is slidably received within the sleeve 16 and is made of a semi-rigid material to permit movement within the arcuate portion of the sleeve and yet not kink upon the application of forces typically associated with the measurement of pocket depths.

In operation, the fiber 18 is held in the fully extended position shown in FIG. 1. The fiber is then inserted into the periodontal pocket between the tooth 20 and the gum 22. Upon contact with the bone 23 at the base of the pocket, the fiber begins to retract into the sleeve 16 and the probe body 12 until the sleeve makes contact with the gum 22. The length of the portion of the fiber which remains at the exterior of the periodontal probe 10 is thereafter equal to the depth of the periodontal pocket. As will be explained more fully below, the periodontal probe 10 generates a signal having a characteristic precisely related to the length of the extracted portion. For purposes of clarity, the wiring among components is omitted in FIGS. 1 and 2.

The probe body 12 has a rearward segment 24 and a forward segment 26. Within the segments 24 and 26 is an internally-threaded member 28 that is attached to an externally-threaded member 30. The threaded members 28 and 30 are slidably received within the tubular probe body 12 to permit detachment of the logic housing 14 and the electrical components within the probe body 12 prior to sterilization of the fiber 18 and the probe body 12.

As best seen in FIG. 2, an annular region 32 of the forward segment 26 is electrically isolated from the rearward segment 24 by an insulator 34. The annular isolated region 32 functions as a trigger for a touch-actuated circuit to be described below. Touch-actuation eliminates the need of operation of a two-position switch which requires application of a significant amount of force at the critical time of depth measurement.

A slider member 36 is coaxially aligned with the probe body 12 and is maintained in position by the internally-threaded member 28. The contact of the slider member 36 and the threaded member 28, as well as the materials chosen in constructing these members, should be designed to minimize the friction during relative movement of the two members. The tip of the slider member 36 is attached to the fiber 18. The axial passage 38 of the probe body 12 is tapered to limit forward motion of the slider member, so that the fiber 18 is in the fully extracted position when the slider member abuts the tapered probe body.

The slider member 36 is biased in the fully extended position by a constant force spring 40. A core 42 is sandwiched between the slider member 36 and the constant force spring 40. Each of the parts 36, 40 and 42 are able to move relative to the probe body. Preferably, the core is an iron-nickel core, but this is not critical. The core, however, should be made of a ferromagnetic material.

The core 42 moves coaxially within a coil winding 44 fixed to the rearward segment 24 of the probe 10. The coil and the coil winding function together as a frequency-variation device of an electro-mechanical transducer. As the fiber 18 is extended from or retracted into the sleeve 16, the core 42 is moved forwardly or rearwardly, respectively The constant force spring 40 biases the core into a predetermined relationship with the coil winding. Axial movement of the core affects the electromagnetic characteristics of the coil winding, thereby affecting the frequency of an oscillator in which the coil is the major inductance of an LC oscillator.

Referring now to FIGS. 1 and 3, connected to the tubular probe body 12 is the logic housing 14 which contains a battery 46 and circuitry for generating and transmitting a signal precisely related to the depth of a periodontal pocket. Briefly, the circuitry includes a touch-actuated switch 48, a transmitter 50 and a "transducer means" which comprises an oscillator 52 and a pulse-forming timer 54. The transmitter 50 controls current pulses through an infrared LED 56 located on the logic housing 14. Finger contact with the touch-actuated switch 48 initiates the timer 54 for pulsed illumination of the infrared LED 56. The timed illuminations, or pulses, are received by a pickup element 58 of a display unit 60. The pickup element 58 is typically a photodetector, but this in not critical It is possible to employ a plurality of pickup elements where the periodontal probe is to be used in more than one office. For example, adjacent offices may employ a duplication of those components of the display unit 60 which allow interface between the display unit and an operator.

In operation, a CPU 62 of the display unit 60 sets the gain of the pickup circuitry 58, and then waits for detection of data. The time interval from the leading edge of one pulse to the leading edge of a second pulse is ascertained. Determination of the time interval permits calculation of the length of the extended portion of the fiber from the periodontal probe, and therefore, the depth of the periodontal pocket. The depth measurement is stored in a memory and is displayed on an LCD display 64. Simultaneously, voice synthesis circuitry 66 and an amplifier 68 provide audibilization of the depth measurement through a speaker 70. Voice synthesis eliminates the need of an operator turning from a patient to visually verify calculation of a depth measurement. Typically, six measurements are taken about the periphery of each tooth. The display unit 60 may prompt the operator with procedural information. The results of depth readings are communicated to a printer via a printer interface 72. If desired, the data can also be stored in a host computer via a computer interface 74. The display unit 60 also includes a keypad 76 to allow an operator to prompt the CPU 62. A power supply 78 provides the required voltage levels for operation of the display unit 60.

FIG. 4 is a schematic diagram of the circuitry housed within the periodontal probe. Included is the touch-actuated switch 48, the transmitter 50, the oscillator 52 and the timer 54. As will be explained more fully below, the timer 54 is a programmable timer and is shown in block form in FIG. 4. The illustrated timer is an MC14536B integrated circuit sold under the trademark Motorola. However, this is not critical.

The output of the touch-actuated switch 48 is at the collector of an NPN transistor 80 and is tied to a clock inhibit 82 of the timer 54. When the touchactuated switch is in a quiescent condition, the output is a high state which inhibits counting by the timer. The switch 48 is a capacitance switch. Placement of a finger on the annular isolated region 32 of the periodontal probe causes a change in capacitance which permits current flow through a trigger transistor 84. The collector of the trigger transistor 84 is connected to the base of the output transistor 80 and the current flow through the trigger transistor results in the clock inhibit 82 moving from a high level to a low level. When the clock inhibit is low, the counter of the timer 54 begins counting on the occurrence of the first negative edge of the oscillator 52.

The oscillator 52 is an LC oscillator and includes a transistor 86, the core 42 and the coil winding 44. As noted above, the core and coil winding are biased into a desired relationship with respect to each other. Movement of the fiber relative to the periodontal probe is translated into movement of the core 42 relative to the coil winding 44. The position of the core 42 affects the inductance of the LC oscillator, thereby affecting frequency. The coil winding is connected to the clock input pin 88 of the timer 54. The base of the transistor 86 is electrically attached to an output pin 90 of the timer to form the LC oscillator. The oscillator 52 supplies a signal to the timer 54, and the signal has a frequency which is precisely related to pocket depth since the resonant frequency depends upon the relative positions of the core 42 and the coil winding 44.

The timer 54 includes a decoder 92 and a monostable multivibrator 94. A resistor 96 ties the monostable circuit 94 in a high state to enable the circuit. The resistor 96 and the timer's internal capacitance determine the minimum output pulse widths. Here, it is desirable to have a pulse width of microseconds. The transmitter 50 includes an emitter follower 98 and the infrared LED 56. Current flow to the infrared LED is controlled by the timer 54 at the decode out pin 100.

In operation, the fiber 1B, shown in FIG. 1, is inserted into the periodontal pocket between the tooth 20 and the gum 22 of a patient. Further downward pressure on the periodontal probe 10 causes the fiber to recede into the sleeve 16 and causes rearward motion of the slider member 36 and the core 42. Upon contact of the sleeve 16 with the gum 22 of the patient, the length of the portion of the fiber still extended from the sleeve is equal to the depth of the periodontal pocket. Referring again to FIG. 4, the oscillator 52 runs continually and provides a signal having a frequency determined by the relative position of the core 42 and the coil winding 44. After an operator is satisfied that the sleeve is in contact with the gum of the patient, the finger of the operator is brought into contact with the annular isolated region 32 on the probe body. The change in capacitance due to such contact is detected by the touch-actuated switch 48 which takes the clock inhibit 82 low. The counter of the timer 54 is thereby initialized. The monostable multivibrator 94 and the resistor 96 produce a high state output pulse width of 5 microseconds. The width of the low state at the decode out pin 100, on the other hand, is dependent upon the frequency of the oscillator 52, which is dependent upon the depth of the periodontal pocket. The output at pin controls the emitter follower 98, allowing current flow through the infrared LED. Preferably, the width of the low state remains in the range of 20-30 microseconds depending upon the relative position of the core 42 and the coil winding 44. When the operator's finger is removed from the annular isolated region 32, the clock inhibit 82 is again brought to a high state to discontinue transmission of data to a remote receiver.

The schematic diagram of FIG. 4 is an exemplary circuit. Other circuits for the transmission of data via an infrared LED are possible. Moreover, it is possible to transmit the necessary data by use of ultrasonic waves or radio frequency transmission.

I claim:

1. An apparatus for determining the depth of an anatomical pocket of a patient comprising,
   a hand-held probe body defining a longitudinal passage therein,
   a movable fiber slidably received within said passage, a pocket-entering end of said fiber extending in a reciprocating manner to the exterior of said probe body,
   transducer means operatively coupled to said fiber for generating a signal having a characteristic related to the depth of an anatomical pocket as determined by the measure of one of the relative position and the relative movement of said pocket-entering end and said probe body, and
   finger-actuated means structurally associated with said probe body for selectively transmitting said signal in a wireless fashion to a remote receiver, said finger-actuating means including a transmitter and an actuation circuit, said actuation circuit having means for actuating said transmitter upon sensing of a change of capacitance associated with said probe body, 2. The apparatus of claim 1 wherein said probe body includes a grip region and includes a trigger region electrically isolated from said grip region, said actuation circuit being in capacitance-sensing communication with said trigger region.

3. The apparatus of claim 1 further comprising said remote receiver, said receiver having means for recording said depth of the anatomical pocket.

4. The apparatus of claim 1 wherein said transmitter includes a light source and a pulseproducing circuit in electrical communication with said transducer means at an input end and in electrical communication with said light source at an output end.

5. The apparatus of claim 4 wherein said light source is an infrared LED.

6. The apparatus of claim 1 wherein said transducer means includes an electro-mechanical transducer having a core and a coil winding, one of said core and said coil winding being in motion transfer engagement with said fiber, the relative position of said core and coil winding determining a signal frequency.

7. An apparatus for determining the depth of an anatomical pocket of a patient comprising,
   a hand-held probe body defining a longitudinal passage therein,
   a movable fiber slidably received within said passage said fiber having a pocket-entering end entending in a reciprocating manner to the exterior of said probe body,
   transducer means operatively coupled to said fiber for generating a signal having a characteristic related to the depth of an anatomical pocket as determined by the measure of one of the relative position and the relative movement of said pocket-entering end and said probe body, and
   finger actuated means structurally associated with said probe body for selectively transmitting said signal in a wireless fashion to a remote receiver, said finger actuating means including a light source and a pulse-producing circuit in electrical communication with said transducer means at an input end and in electrical communication with said light source at an output end, said pulse-producing circuit including a timer, said timer generating pulses to said light source in accord with said signal.

8. A periodontal probe for determining the depth of an anatomical pocket, comprising,
   a tubular housing having a sleeve at a forward end,
   a semi-rigid probing member slidably received in said sleeve, said probing member having an extreme extended position in which a lead portion of said probing member extends from said sleeve,
   an electro-mechanical transducer means attached to said housing and operatively coupled to said probing member for generating a signal having a signal characteristic related to the measure of extension of said lead portion from said sleeve, a transmitter connected to said housing, said transmitter having an input electrically coupled to said transducer means and having an output means for wireless radiation of waves having a wave characteristic corresponding to said signal characteristic, and finger-contact trigger means associated with said housing for selectively actuating said wireless radiation of waves, said trigger means being a capacitance-sensing trigger.

9. The periodontal probe of claim 8 wherein said transmitter includes a light source and means for pulsing illumination of said light source in accord with said wave characteristic.

10. The periodontal probe of claim 9 wherein said light source is an infrared LED.

11. The periodontal probe of claim 8 wherein said housing has an electrically isolated region and wherein said capacitance-sensing trigger is in electrical communication with said isolated region.

12. The periodontal probe of claim 8 further comprising a timer, said electrical coupling of said transducer to said transducer being via said timer, said timer generating pulses corresponding to said signal characteristic, said signal characteristic being signal frequency.

13. An apparatus for determining the depth of a periodontal pocket comprising, a hand-held probe body defining a longitudinal passage open at a forward end of said probe body, a fiber having a rearward portion slidably received in said passage and having a forward, pocketentering portion extending therefrom, said forward portion having a lead end, transducer means for generating a signal having a signal characteristic corresponding to the position of said lead end relative to said probe body, said transducer means including a core and a coil winding housed within said probe body, one of said core and said coil winding being fixed to said probe body and the other one being in motion-transfer engagement with said fiber, spring means within said probe body for exerting a constant force to bias said fiber forwardly, a transmitter connected to said probe body, said transmitter having an input coupled to receive said signal from said transducer means and having means for wireless radiation of waves having a wave characteristic related to said signal characteristic, and a touch-actuated means for triggering said radiation of waves, said touch-actuated means being a capacitance switch disposed at the exterior of said probe body.

14. The apparatus of claim 13 further comprising a receiver means for converting the energy emitted by said transmitter into an indication of the depth of said periodontal pocket.

15. The apparatus of claim 14 wherein said receiver means includes voice synthesization of said indication of depth.

16. The apparatus of claim 14 wherein said receiver includes a digital readout of said indication of depth.

17. The apparatus of claim 13 wherein said means for wireless radiation includes a light source, said touchactuated means triggering recurring illumination of said light source in a manner related to said signal characteristic.

* * * * *

UNITED STATES PATENT AND TRADEMARK OFFICE
CERTIFICATE OF CORRECTION

PATENT NO. : 4,960,132

DATED : October 2, 1990

INVENTOR(S) : Charles F. Habekost

It is certified that error appears in the above-identified patent and that said Letters Patent is hereby corrected as shown below:

Column 1, line 39, "depthmeasuring" should read
  -- depth-measuring --.

Column 3, lin 59, "respectively The" should read
  -- respectively. The --.

Column 4, line 11, "critical It is" should read
  -- critical. It is --.

Column 4, line 51, "touchactuated" should read
  -- touch-actuated --.

Column 5, line 18, "width of microseconds" should read
  -- width of 5 microseconds --.

Column 5, line 22, "fiber 1B" should read -- fiber 18 --.

Column 5, line 46, "pin controls" should read
  -- pin 100 controls --.

UNITED STATES PATENT AND TRADEMARK OFFICE
CERTIFICATE OF CORRECTION

PATENT NO. : 4,960,132

DATED : October 2, 1990

INVENTOR(S) : Charles F. Habekost

It is certified that error appears in the above-identified patent and that said Letters Patent is hereby corrected as shown below:

Claim 4, column 6, line 4, "pulseproducing circuit" should read
-- pulse-producing circuit --.

Claim 12, column 7, line 27, "said transducer" should read
-- said transmitter --.

Claim 13, column 7, line 37, "pocketentering" should read
-- pocket-entering --.

Claim 17, column 8, lines 33-34, "touchactuated" should read
-- touch-actuated --.

Signed and Sealed this

Fourth Day of February, 1992

*Attest:*

HARRY F. MANBECK, JR.

*Attesting Officer*   Commissioner of Patents and Trademarks